United States Patent
Chern et al.

[11] Patent Number: 6,136,838
[45] Date of Patent: Oct. 24, 2000

[54] SULFURPENTAFLUOROPHENYLPYRAZOLES FOR CONTROLLING ECTOPARASITIC INFESTATIONS

[75] Inventors: Rey T. Chern, Harteyville, Pa.; Jeffrey N. Clark, Middletown, N.J.; Marlene D. Drag, Wellsville, Mo.; Joel R. Zingerman, Doylestown, Pa.

[73] Assignee: Merck & Co., Inc., Rahway, N.J.

[21] Appl. No.: 09/271,092

[22] Filed: Mar. 18, 1999

Related U.S. Application Data

[60] Provisional application No. 60/078,639, Mar. 19, 1998.

[51] Int. Cl.[7] .................................................. A61K 31/415
[52] U.S. Cl. ............................................................ 514/404
[58] Field of Search .............................................. 514/404

[56] References Cited

U.S. PATENT DOCUMENTS

| | | | |
|---|---|---|---|
| 5,015,630 | 5/1991 | Fisher et al. | 514/30 |
| 5,451,598 | 9/1995 | Salmon | 514/404 |
| 5,478,855 | 12/1995 | Suzuki et al. | 514/374 |
| 5,637,607 | 6/1997 | Pilato et al. | 514/404 |
| 5,639,771 | 6/1997 | Obata et al. | 514/374 |

FOREIGN PATENT DOCUMENTS

| | | |
|---|---|---|
| 0 357 460 | 3/1990 | European Pat. Off. . |
| 0 382 173 | 8/1990 | European Pat. Off. . |
| 0 444 964 | 9/1991 | European Pat. Off. . |
| 0 503 538 | 9/1992 | European Pat. Off. . |
| 0 594 291 | 4/1994 | European Pat. Off. . |
| 0 626 375 | 11/1994 | European Pat. Off. . |
| 195 20 936 | 12/1996 | Germany . |
| WO 93/19053 | 9/1993 | WIPO . |
| WO 93/25543 | 12/1993 | WIPO . |
| WO 94/15944 | 7/1994 | WIPO . |
| WO 94/19334 | 9/1994 | WIPO . |
| WO 95/22552 | 8/1995 | WIPO . |
| WO 96/11945 | 4/1996 | WIPO . |
| WO 96/15121 | 5/1996 | WIPO . |
| WO 97/12521 | 4/1997 | WIPO . |

*Primary Examiner*—Kevin E. Weddington
*Attorney, Agent, or Firm*—Shu M. Lee; David L. Rose

[57] ABSTRACT

Sulfurpentafluorophenylpyrazoles of formula I are highly potent against flea and tick infestations in animals. The compounds may be formulated to provide products with long duration of action and low potential for inducing vomition and other adverse reactions in treated animals.

29 Claims, 1 Drawing Sheet

SULFURPENTAFLUOROPHENYLPYRAZOLES FOR CONTROLLING ECTOPARASITIC INFESTATIONS

CROSS REFERENCE TO RELATED APPLICATIONS

This application is based on and claims priority from U.S. provisional application No. 60/078,639, filed Mar. 19, 1998, which is hereby incorporated by reference in its entirety.

SUMMARY OF THE INVENTION

The present invention concerns a method for controlling ectoparasitic infestation using highly potent compounds, a long acting injectable formulation of such compounds which provides an unexpected long duration of efficacy, and a method for administering said compounds while avoiding or reducing the side effects that may occur with such compounds. Additional objects will become apparent from a reading of the following description.

BACKGROUND OF THE INVENTION

Blood sucking parasitic infestation on animals, especially the infestation of pets by fleas, has been a continued problem in the art. Infestation of dogs and cats with fleas may cause local irritation or annoying scratching. Intense scratching can lead to open wounds that can become infected with bacteria.

Many different types of flea deterring or larvicide or adulticide treatments have been developed in attempts to rid animals of fleas. A variety of products have been marketed for controlling flea infestation in household pets such as dogs, cats, hamsters, etc. Most products contain harsh chemicals that can have serious consequences when used too often or in excess of recommended quantities. Typical of these chemicals are propoxur (o-isopropoxphenyl), methyl carbamate, diazinon, chlorpyrifos, d-limonene, cyano(3-phenoxypheny)methyl 4-chloro-alpha (1-methylethyl) benzeneacetate, pyrethrins, piperonyl butoxide and N-octyl bicycloheptane dicarboximide. Although these chemicals are generally effective against fleas if used carefully, they can often have serious side effects. Flea resistance to these compounds has also been seen in the field. Many products may excessively dry the skin or cause eczema or allergic reactions in some animals. Skin wounds caused by the animal's scratching at fleas can become infected and the infections are often aggravated by these chemicals. Many of these chemicals cannot be applied to the fur of animals, such as cats, that self-groom by licking the skin and fur. Persons applying these flea killing chemicals to animals must often be very careful to avoid excessive contact with them. Those grooming animals are advised to wear rubber gloves to avoid continuous contact with the chemicals. Care must be exercised to keep the chemicals out of the eyes and away from the mucus membranes of both the animal and the person applying them. Breathing vapor from the chemicals over long periods must also be avoided. Many of these chemicals are not rapidly biodegradeable and constitute an environmental hazard if misused. Thus, there is a continuing need for improved and fully effective materials that can be applied to fur bearing animals to eliminate fleas while being environmentally benign, and avoiding deleterious side effects.

1-(4-$SF_5$-phenyl)pyrazoles of formula I are known compounds reportedly to be useful as insecticides (see U.S. Pat. No. 5,451,598). They have not been disclosed as useful in controlling ectoparasites, such as flea and tick infestations in animals.

PCT Published Application WO97/12521 discloses ready-to-use solutions for topical application against fleas and ticks containing as active ingredient a compound of the formula 1:

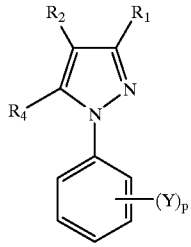

wherein Y may be halogen or $SF_5$, among others, and p may be from 1 to 5. The only active compound specifically exemplified in the claimed ready-to-use solution is the compound fipronil 2:

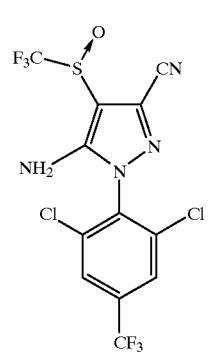

Fipronil is commercially available in topical formulations against fleas and ticks. It has been known to cause vomition in animals when administered systemically. Topical application of fipronil provides efficacy for not more than three months.

The present inventors have found that certain $SF_5$-phenylpyrazoles are highly potent agents against fleas and ticks. More particularly these $SF_5$-phenylpyrazoles exhibit higher potency than fipronil against fleas. The $SF_5$-phenylpyrazoles may be formulated for systemic administration to provide efficacy against fleas and/or ticks for extended period while avoiding or reducing the potential of vomition and/or other adverse reactions in treated animals.

DETAILED DESCRIPTION OF THE INVENTION

Figure 1:
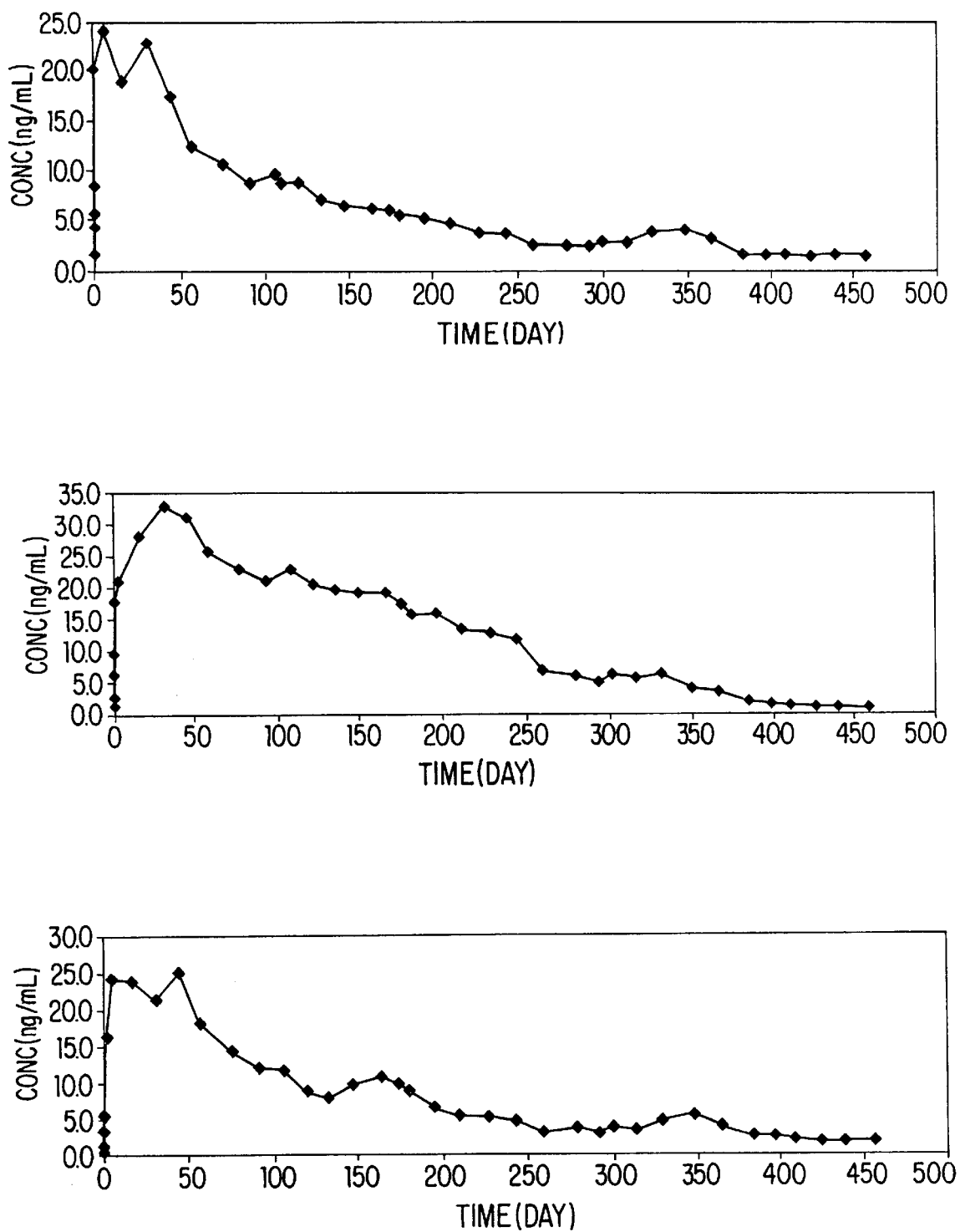
FIG. 1 depicts plasma levels of 6-amino-3-cyano-1-(2,6-dichloro-4-sulfurpentafluorophenyl)-4-(trifluoromethylthio) pyrazole in dogs treated with the formulation of Example 1.

The present invention provides for a method of controlling ectoparasitic infestation in a companion animal which comprises administering to said animal a therapeutically effective amount of a compound of formula I:

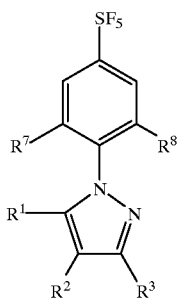

I wherein
R$^1$ is hydrogen, halogen, or a group NR$^4$R$^5$;
R$^2$ is —S(O)$_n$R$^6$;
R$^3$ is —CN or CX—NY$^1$Y$^2$;
R$^4$ and R$^5$ are independently hydrogen or alkyl;
R$^6$ is haloalkyl;
R$^7$ and R$^8$ are independently halogen;
X is O or S;
Y$^1$ and Y$^2$ are independently hydrogen, nitro, amino, or alkyl optionally substituted by halogen, cycloalkyl, formyl, C$_{2-7}$ alkanoyl, C$_{4-7}$ cycloalkylcarbonyl, C$_{2-7}$ alkoxycarbonyl, C$_{2-7}$ haloalkoxycarbonyl, aryl, or aromatic heterocyclic group; or
Y$^1$ and Y$^2$ together with the nitrogen to which they are attached form an aliphatic heterocyclic group containing from 4 to 8 ring atoms and optionally substituted by halogen or alkyl; or
Y$^1$ and Y$^2$ together form the group=CHY$^3$; or
Y$^1$ is hydrogen and Y$^2$ is alkoxycarbonyl, alkylcarbonyl, optionally substituted aralkyl, or —S(O)nR$^6$;
Y$^3$ is alkyl, C$_{2-6}$ alkenyl, aryl, an aromatic heterocycle, or amino optionally substituted by halogen;
n is 0, 1 or 2; or
a pharmaceutically acceptable salt thereof.

Another aspect of the present invention provides a method of controlling ectoparasitic infestation in a companion animal while avoiding or reducing the potential of vomition and/or other adverse reactions which comprises administering systemically to said animal a therapeutically effective amount of a compound of formula I in a formulation that provides peak plasma level of the administered compound lower than about 100 ng/ml.

Another aspect of the present invention provides a pharmaceutical composition for injection which comprises:
(1) a compound of formula I;
(2) a biologically acceptable polymer; and
(3) a lipophilic solvent.

Another aspect of the present invention provides a method of controlling ectoparasitic infestation in a companion animal while avoiding or reducing the potential of vomition and/or other adverse reactions which comprises injecting said animal with a pharmaceutical composition comprising:
(1) a compound of formula I;
(2) a biologically acceptable polymer; and
(3) a lipophilic solvent.

In one subset of compounds of formula I R$^1$ is halogen (such as bromine) or a group NR$^4$R$^5$ (such as NH$_2$).

In another subset of compounds of formula I R$^3$ is CN.

In another subset of compounds of formula I R$^2$ is S(O)$_n$R$^6$ wherein R$^6$ is halomethyl (such as trifluoromethyl) or haloethyl (such as 1,1-difluoroethyl).

In another subset of compounds of formula I R$^7$ and R$^8$ are independently chloro.

In a preferred embodiment the ectoparasite to be controlled is flea or tick, more preferably flea.

In another preferred embodiment the compound of formula I is administered parenterally.

In another preferred embodiment the methods and pharmaceutical compositions of the present invention employ compounds of formula Ia:

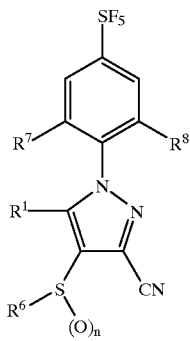

Ia wherein
R$^1$ is halogen or NR$^4$R$^5$;
R$^4$ and R$^5$ are independently hydrogen or C$_{1-4}$ alkyl;
R$^6$ is C$_{1-4}$ haloalkyl;
R$^7$ and R$^8$ are independently chloro or bromo; and
n is 0, 1 or 2.

A more preferred embodiment of the present methods and pharmaceutical compositions employs compounds of formula Ia wherein
R$^1$ is bromo or NR$^4$R$^5$;
R$^4$ and R$^5$ are independently hydrogen or methyl; and
R$^6$ is halomethyl or haloethyl.

Representative compounds of formula I suitable for use in the present methods or pharmaceutical compositions include:
(1) 6-amino-3-cyano-1-(2,6-dichloro-4-sulfurpentafluorophenyl)-4-(trifluoromethylthio)pyrazole;
(2) 6-amino-3-cyano-1-(2,6-dichloro-4-sulfurpentafluorophenyl)-4-(trifluoromethylsulfinyl)pyrazole;
(3) 6-amino-3-cyano-1-(2,6-dichloro-4-sulfurpentafluorophenyl)-4-(trifluoromethylsulfonyl)pyrazole;
(4) 6-amino-3-cyano-1-(2,6-dichloro-4-sulfurpentafluorophenyl)-4-(1,1-difluoroethylthio)pyrazole; and
(5) 6-bromo-3-cyano-1-(2,6-dichloro-4-sulfurpentafluorophenyl)-4-(trifluoromethylthio)pyrazole.

In another preferred embodiment the pharmaceutical composition for injection further comprises a hydrophilic solvent.

The term "alkyl" as used herein includes straight or branched chain alkyl groups, preferably containing up to 6 carbon atoms. This applies also to alkyl moieties contained in other groups such as "haloalkyl" groups. The term "cycloalkyl" used herein refers to a carbocyclic ring suitably having from 3 to 10 and preferably from 3 to 7 carbon atoms in the ring.

The term "halogen" includes fluorine, chlorine, bromine and iodine.

The term "systemic administration" includes oral and parenteral administration.

The term "companion animal" includes dogs and cats.

The term "controlling" includes preventing (e.g. prophylactic use), treating, eradicating, ameliorating or otherwise reducing the severity of the condition being controlled.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I and the other specified components that comprise the carrier.

The term "pharmaceutical composition" is intended to mean a composition suitable for use in veterinary medicine. The term "pharmaceutically acceptable" is intended to mean acceptable for use in animals, particularly in companion animals such as dogs and cats.

"Biologically acceptable polymer" can be any biologically acceptable polymer, such as a biologically acceptable polymer recognized in the art. For instance, the biologically acceptable polymer can have one or more or all of the following characteristics: be bioerodible by cellular action, biodegradable by action of non-living body fluid components, soften when exposed to heat but return to the original state when cooled and are capable of substantially dissolving or dispersing in a water-miscible carrier or solvent to form a solution or dispersion. Upon contact with an aqueous fluid and the polymer are capable of assisting in the formation of the film coated or encapsulated liquid. The kinds of polymers suitable for the present composition generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malicacid), poly (amino acids), poly(methyl vinyl ether), poly(maleic anhydride), chitin, chitosan, and copolymers, terpolymers, or combinations or mixtures therein. Polylactides, polycaprolactones, polyglycolides and copolymers thereof are preferred polymers, with poly(lactide-co-glycolide) copolymer ("PLGA") highly preferred.

"Poly(lactide-co-glycolide)" means a copolymer of lactic and glycolic acids having a lactide:glycolide ratio of from 95:05 to 50:50, preferably 75:25 to 65:35. The lactic acid can be d- or l- or dl-. The copolymer may be a single copolymer of a mixture of copolymers within the above-defined parameters.

"Hydrophilic solvent" means water miscible solvents, preferably those when mixed with water in a ratio from 1:9 to 9:1 form a single-phase solution. For example, propylene glycol, polyglycols such as polyethylene glycol 200, polyethylene glycol 300 and polyethylene glycol 400, di(ethylene glycol)ethyl ether (Transcutol), isopropylidene glycerol (Solketal), dimethyl isosorbide, propylene carbonate, glycerol, glycerol formal, glycofural, pyrrolidones such as N-methyl pyrrolidone and 2-pyrrolidone, di(propyleneglycol) methyl ether, and mixtures thereof. Other solvents may also be useful as the hydrophilic solvent.

For instance, the hydrophilic solvent can be a $C_2$ to $C_6$ alkanol (e.g., ethanol, propanol, butanol), acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, and 1-dodecylazacycloheptan-2-one. The hydrophilic solvent can be a mixture of solvents.

"Lipophilic solvent" means water immiscible solvents, preferably with a solubility in water of less than 10% at room temperature. Lipophilic solvent may be triethyl citrate, Miglyol 812, Miglyol 840, Crodamol GTCC, triacetin, triethyl citrate or benzyl benzoate; and additional lipophilic solvents may be used, e.g., hydrophobic rate modifying agents or plasticizers such as fatty acids, triglycerides, triesters of glycerol, oils such as castor oil, soybean oil or other vegetable oils or derivatives thereof such as epoxidized or hydrogenated vegetable oils such as epoxidized soybean oil or hydrogenated castor oil, sterols, higher alkanols (e.g., $C_6$ or higher), glycerin and the like. The lipophilic solvent can be a mixture of solvents.

Compounds of formula I are highly potent agents against ectoparasites, particularly fleas and ticks, and especially fleas. Thus compounds of formula I have utility for controlling ectoparasitic infestations in animals, particularly in companion animals such as dogs and cats. Preferably compounds of formula I are used for controlling flea infestation in dogs.

Compounds of formula I may be administered in formulations wherein the active compound is intimately admixed with one or more inert ingredients and optionally including one or more additional active ingredients. The compounds may be used in any composition known to those skilled in the art for systemic administration to animals. For application to animals to control ectoparasites, oral formulations, in solid or liquid or parenteral liquid, implant or depot injection forms may be used.

The optimum amount to be employed for best results will, of course, depend upon the particular compound employed, the species of animal to be treated, the route and formulation of administration, and the type and severity of parasitic infection or infestation. Generally good results are obtained with compounds of formula I when administered from about 0.1 to 50 mg per kg of animal body weight, such total dose being given at one time or in divided doses over a relatively short period of time such as 1–5 days.

Compounds of formula I may be administered orally in a unit dosage form such as a capsule, bolus or tablet including chewable tablet. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat.

Compounds of formula I may be administered to animals parenterally, for example, by intraruminal, intramuscular, intravascular, intratracheal, or subcutaneous injection in which the active ingredient is dissolved or dispersed in a liquid carrier vehicle. Parenteral vehicle may be of the vegetable oil variety (e.g. peanut oil, cotton seed oil, propylene glycerol octanoate decanoate and the like). Other parenteral vehicles such as organic preparation using triacetin, benzyl benzoate, solketal, glycerol formal, propylene glycol, and aqueous parenteral formulations are also used. The active compound or compounds are dissolved or suspended in the parenteral formulation for administration; such formulations generally contain from 0.0005 to 20% by weight of the active compound. A preferred parenteral formulation is described hereinbelow.

Compounds of the present invention may be co-administered or used with other anthelmintic agents. These anthelmintic agents are meant to include, but not be restricted to, compounds selected from the avermectin and milbemycin class of compounds such as ivermectin, avermectin, abamectin, emamectin, eprinomectin, doramectin, milbemycin derivatives described in EPO 357460, EPO 444964 and EPO 594291, moxidectin, Interceptor™ and nemadectin. Additional anthelmintic agents include the benzimidazoles such as thiabendazole, cambendazole, parbendazole, oxibendazole, mebendazole, flubendazole, fenbendazole, oxfendazole, albendazole, cyclobendazole, febantel, thiophanate and the like. Additional anthelmintic agents include imidazothiazoles and tetrahydropyrimidines such as tetramisole-levamisole, butamisole, pyrantel, pamoate, oxantel or morantel.

Compounds of this invention may be co-administered or used in combination with fipronil (FRONTLINE™); or with an insect growth regulator with molt inhibiting activity such as lufenuron (PROGRAM™) and the like; or with ecdysone agonists such as tebufenozide and the like, which induces premature molt and causes feeding to cease; or with imidacloprid (ADVANTAGE™).

Compounds of this invention may be co-administered or used in combination with avermectin or milbemycin or doramectin derivatives such as those described in U.S. Pat. No. 5,015,630, WO 94/15944, WO95/22552.

Compounds of this invention may be co-administered or used in combination with cyclic depsipeptides that exhibit anthelmintic efficacy such as those described in WO96/11945, WO93/19053, WO93/25543, EP 626375, EP 382173, WO 94/19334, EP 382173 and EP 503538.

Compounds of this invention may be co-administered or used in combination with nodulisporic acid derivatives such as those described in PCT Application WO96/29073.

Compounds of this invention may be used in combination or be co-administered with derivatives and analogs of the general class of dioxomorpholine antiparasitic and anthelmintic agents as illustrated by WO 9615121; or with pyrethroids or organophosphates or insecticidal carbamates, such as those described in "Chemotherapy of Parasitic Diseases", Campbell, W. C. and Rew, R. S, Eds., 1986; or with derivatives and analogs of the general class of paraherquamide and macfortine anthelmintic agents, as well as oxazoline anthelmintics and insecticides such as those disclosed in U.S. Pat. Nos. 5,478,855, 4,639,771 and DE 19520936.

The co-administered compounds are given via routes and in doses that are customarily used for those compounds. These compounds may also be included as a second active ingredient in compositions containing the sulfurpentafluorophenylpyrazoles of the present invention.

The present inventors have further discovered that compounds of formula I may be administered systemically while avoiding or reducing the potential of vomition and/or other adverse reactions in treated animals when the peak plasma level of the administered active compound is kept below about 100 ng/ml. Depending on the specific compound, route of administration, formulation, the peak plasma level may be kept below the target level when the dose administered ranges from about 0.05 mg/kg to about 50 mg/kg. In general oral dosage of about 0.5 mg/kg to about 3 mg/kg and parenteral dosage of about 1 mg/kg to about 20 mg/kg may be used.

Another aspect of the present invention provides for a long-acting injectable composition containing a compound of formula I which provides efficacy in controlling ectoparasitic infestation in animals for at least six months after a single injection while avoiding or reducing the potential of vomition and/or other adverse reactions in treated animals. This long-acting injectable composition comprises: 1) a compound of formula I, 2) a biologically acceptable polymer, and 3) a lipophilic solvent. In a preferred embodiment, the biologically acceptable polymer is poly (lactide/glycolide) copolymer. In another preferred embodiment the composition further comprises a hydrophilic solvent.

In the long-acting injectable composition, poly(lactide/glycolide) copolymers with lactide/glycolide ratio in the range of 95/5 to 50/50, molecular weight in the range of 2,000 to 100,000 are suitable; preferably the lactide:glycolide ratio is from 75:25 to 65:35.

The lipophilic solvent includes but is not limited to triacetin, propylene glycerol octanoate decanoate, benzyl benzoate, ethyl oleate, other vegetable oils and derivatives, and triethyl citrate, and mixtures thereof. The hydrophilic solvent includes, but is not limited to, glycerol formal, glycofural, N-methyl pyrrolidone, 2-pyrrolidone, isopropylidene glycerol, di(propylene glycol) methyl ether, and mixtures thereof.

The active compound is present in the composition in amounts ranging from about 1% w/v to about 30% w/v; preferably 1 to 10%, and more preferably 5 to 10%. The polymer is present in amount ranging from about 1 to about 20% w/v; preferably about 1 to about 10% w/v, and more preferably 5 to 10%. Preferably, the weight ratio of the copolymer to the active compound is less than or equal to 1:1; for example about 0.3:1 to 1:1. The lipophilic vehicle is present in about 10 to about 100% v/v, preferably from about 20 to about 90%, with the balance being made up of the hydrophilic vehicle.

The long-acting injectable composition may be prepared by dissolving all the solid ingredients in the vehicle under normal manufacturing conditions used for sterile injectable products. The present composition may contain additional inert substances commonly used in parenteral formulations including, but not limited to, antimicrobial agents, antioxidants, etc, as well as additional active ingredients such as those described above as being suitable for combination with compounds of formula I.

The long-acting injectable composition is capable of maintaining systemic drug concentration at a relatively constant level, and avoiding "burst" delivery, over a prolonged period of time that can be more than six months. Thus it is especially suitable for the delivery of compounds of formula I where sharp peak drug plasma levels, which may be over 100 ng/ml, are preferably avoided to minimize potential for vomition and/or other adverse reactions. Accordingly, the present invention further contemplates a method of controlling ectoparasitic infestation in a companion animal while avoiding or reducing the potential of vomition in the treated animals which comprises injecting said animal with a long-acting injectable composition as described above. The method is particularly useful for controlling flea infestation in dogs.

The following examples are provided to illustrate the invention and are not to be construed as limiting the scope of the invention in any manner.

EXAMPLE 1

Preparation of long-acting injectable formulation containing 6-amino-3-cyano-1-(2,6-dichloro-4-sulfurpentafluorophenyl)-4-(trifluoromethylthio)pyrazole Poly(DL-lactide/glycolide) 75/25 (PLGA, 0.25 g) was dissolved in sufficient glycerol formal to provide a 2.5 ml solution. In a separate flask poly(DL-lactide/glycolide) 75/25 (0.25 g) was dissolved in sufficient triacetin to provide a 2.5 ml solution. The two PLGA solutions were mixed well and added to a flask containing the active ingredient (0.50 g). The contents of the flask were mixed until the active ingredient dissolved, and the resulting solution was sterile filtered into a vial and sealed.

EXAMPLE 2

Activity of 6-amino-3-cyano-1-(2,6-dichloro-4-sulfurpentafluorophenyl)-4-(trifluoromethylthio)pyrazole against fleas in dogs Beagle dogs of both sexes 21 to 31 months old and weighing from 10 to 16 kg were used. Groups of three dogs each were treated with the same active compound in different formulations as follows:

Group 1: topical formulation containing 10% w/v of active compound, 5% w/v polyvinylpyrrolidone 30 and ethanol qs to 100% v/v dosed at 5 mg/kg.

Group 2: long acting parenteral formulation containing 10% w/v of the active compound, 25% w/v of sucrose octaacetate, 1% w/v of propylene glycol octanoate decanoate and triacetin qs 100% v/v dosed subcutaneously at 10 mg/kg.

Group 3: long acting parenteral formulation containing 10% w/v active compound, 10% w/v poly(DL-lactide/glycolide)75/25, and qs 100% v/v 1:1 glycerol formal/triacetin dosed at 10 mg/kg subcutaneously.

Control group of three untreated dogs was included.

Treatments were administered once on Day 0. On Day 1 animals all animals were infested with approximately 100 fleas. Animals were combed and fleas counted and removed approximately 48 hours after infestation. Animals were infested on days 12 and 26, and combed and fleas counted and removed approximately 48 hours after infestation. Infestation/counting were repeated approximately monthly until efficacy fell below 80% [% efficacy=(1−(mean flea count of treatment group÷mean flea count of control group)×100).

Blood samples were collected from animals in treatment groups on Day 0 at 1, 2, 3 and 6 hours after treatment, on Day 1 at 24 hours after treatment, and whenever emesis was observed. Blood samples were also collected when flea counts were determined. Animals were observed hourly for 6 hours post treatment for emesis.

The active compound provided >90% efficacy against fleas for between 55 and 90 days in animals in group 1. For animals in group 2>90% efficacy was maintained for up to between 5 and 6 months. For animals in group 3 close to 100% efficacy has been demonstrated for >12 months.

Vomition occurred in group 2 where peak plasma levels were >100 ng/ml. No vomition was observed in group 3. Plasma drug levels of dogs in group 3 are shown in FIG. 1.

What is claimed is:

1. A method for controlling ectoparasitic infestation in a companion animal which comprises administering to said animal a therapeutically effective amount of a compound of formula I:

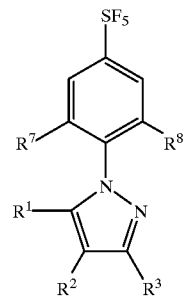

wherein $R^1$ is hydrogen, halogen, or a group $NR^4R^5$;

$R^2$ is —S(O)$_n R^6$;

$R^3$ is —CN or CX—NY$^{12}$;

$R^4$ and $R^5$ are independently hydrogen or alkyl;

$R^6$ is haloalkyl;

$R^7$ and $R^8$ are independently halogen;

X is O or S;

$Y^1$ and $Y^2$ are independently hydrogen, nitro, amino, or alkyl optionally substituted by halogen, cycloalkyl, formyl, $C_{2-7}$ alkanoyl, $C_{4-7}$ cycloalkylcarbonyl, $C_{2-7}$ alkoxycarbonyl, $C_{2-7}$ haloalkoxycarbonyl, aryl, or aromatic heterocyclic group; or $Y^1$ and $Y^2$ together with the nitrogen to which they are attached form an aliphatic heterocyclic group containing from 4 to 8 ring atoms and optionally substituted by halogen or alkyl; or $Y^1$ and $Y^2$ together form the group=$CHY^3$; or $Y^1$ is hydrogen and $Y^2$ is alkoxycarbonyl, alkylcarbonyl, optionally substituted aralkyl, or —S(O)n$R^6$;

$Y^3$ is alkyl, $C_{2-6}$ alkenyl, aryl, an aromatic heterocycle, or amino optionally substituted by halogen;

n is 0, 1 or 2; or a pharmaceutically acceptable salt thereof.

2. A method of claim 1 wherein said compound has formula Ia:

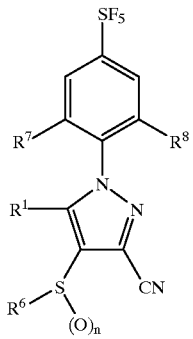

wherein $R^1$ is halogen or $NR^4R^5$;

$R^4$ and $R^5$ are independently hydrogen or $C_{1-4}$ alkyl;

$R^6$ is $C_{1-4}$ haloalkyl;
$R^7$ and $R^8$ are independently chloro or bromo; and
n is 0, 1 or 2.

3. A method of claim 2 wherein
$R^1$ is bromine or $NR^4R^5$;
$R^4$ and $R^5$ are independently hydrogen or methyl; and
$R^6$ is halomethyl or haloethyl.

4. A method of claim 1 wherein said compound of formula I is selected from the group consisting of:
(1) 6-amino-3-cyano-1-(2,6-dichloro-4-sulfurpentafluorophenyl)-4-(trifluoromethylthio)pyrazole;
(2) 6-amino-3-cyano-1-(2,6-dichloro-4-sulfurpentafluorophenyl)-4-(trifluoromethylsulfinyl)pyrazole;
(3) 6-amino-3-cyano-1-(2,6-dichloro-4-sulfurpentafluorophenyl)-4-(trifluoromethylsulfonyl)pyrazole;
(4) 6-amino-3-cyano-1-(2,6-dichloro-4-sulfurpentafluorophenyl)-4-(1,1-difluoroethylthio)pyrazole; and
(5) 6-bromo-3-cyano-1-(2,6-dichloro-4-sulfurpentafluorophenyl)-4-(trifluoromethylthio)pyrazole.

5. A method of any of claims 1 to 4 wherein said ectoparasite is flea.

6. A method of any of claims 1 to 4 wherein said compound of formula I is adminstered parenterally.

7. A method of controlling ectoparasitic infestation in a companion animal while avoiding or reducing the potential of vomition which comprises administering systemically to said animal a therapeutically effective amount of a compound of formula I in a formulation that provides peak plasma level of the administered compound of lower than about 100 ng/ml.

8. A method of claim 7 wherein said compound has formula Ia:

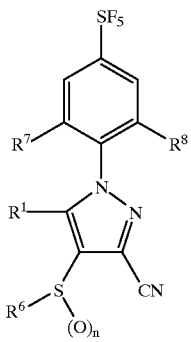

Ia wherein
$R^1$ is halogen or $NR^4R^5$;
$R^4$ and $R^5$ are independently hydrogen or $C_{1-4}$ alkyl;
$R^6$ is $C_{1-4}$ haloalkyl;
$R^7$ and $R^8$ are independently chloro or bromo; and
n is 0, 1 or 2.

9. A method of claim 8 wherein
$R^1$ is bromine or $NR^4R^5$;
$R^4$ and $R^5$ are independently hydrogen or methyl; and
$R^6$ is halomethyl or haloethyl.

10. A method of claim 7 wherein said compound of formula I is selected from the group consisting of:

(1) 6-amino-3-cyano-1-(2,6-dichloro-4-sulfurpentafluorophenyl)-4-(trifluoromethylthio)pyrazole;
(2) 6-amino-3-cyano-1-(2,6-dichloro-4-sulfurpentafluorophenyl)-4-(trifluoromethylsulfinyl)pyrazole;
(3) 6-amino-3-cyano-1-(2,6-dichloro-4-sulfurpentafluorophenyl)-4-(trifluoromethylsulfonyl)pyrazole;
(4) 6-amino-3-cyano-1-(2,6-dichloro-4-sulfurpentafluorophenyl)-4-(1,1-difluoroethylthio)pyrazole; and
(5) 6-bromo-3-cyano-1-(2,6-dichloro-4-sulfurpentafluorophenyl)-4-(trifluoromethylthio)pyrazole.

11. A method of any of claims 7 to 10 wherein said ectoparasite is flea.

12. A method of any of claims 7 to 10 wherein said compound of formula I is adminstered parenterally.

13. A pharmaceutical composition for injection which comprises:
(1) a compound of formula I;
(2) a biologically acceptable polymer; and
(3) a lipophilic solvent.

14. A composition of claim 13 wherein said compound has formula Ia:

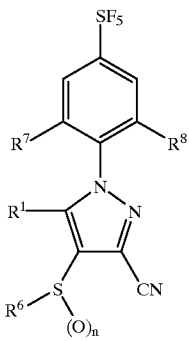

Ia wherein
$R^1$ is halogen or $NR^4R^5$;
$R^4$ and $R^5$ are independently hydrogen or $C_{1-4}$ alkyl;
$R^6$ is $C_{1-4}$ haloalkyl;
$R^7$ and $R^8$ are independently chloro or bromo; and
n is 0, 1 or 2.

15. A composition of claim 14 wherein
$R^1$ is bromine or $NR^4R^5$;
$R^4$ and $R^5$ are independently hydrogen or methyl; and
$R^6$ is halomethyl or haloethyl.

16. A composition of claim 13 wherein said compound of formula I is selected from the group consisting of:
(1) 6-amino-3-cyano-1-(2,6-dichloro-4-sulfurpentafluorophenyl)-4-(trifluoromethylthio)pyrazole;
(2) 6-amino-3-cyano-1-(2,6-dichloro-4-sulfurpentafluorophenyl)-4-(trifluoromethylsulfinyl)pyrazole;
(3) 6-amino-3-cyano-1-(2,6-dichloro-4-sulfurpentafluorophenyl)-4-(trifluoromethylsulfonyl)pyrazole;
(4) 6-amino-3-cyano-1-(2,6-dichloro-4-sulfurpentafluorophenyl)-4-(1,1-difluoroethylthio)pyrazole; and (5) 6-bromo-3-cyano-1-(2,6-dichloro-4-sulfurpentafluorophenyl)-4-(trifluoromethylthio)pyrazole.

17. A composition of claim 13 which comprises:
(1) 1% to 30% of a compound of formula I;
(2) 1% to 20%% w/v of a biodegradable poly (lactide/glycolide) copolymer;
(3) 0 to 90 v/v of a hydrophilic solvent; and
(4) 100 to 10 v/v of a lipophilic solvent.

18. A composition of claims 14 which comprises:
(1) 1% to 30% of a compound of formula Ia;
(2) 1% to 20%% w/v of a biodegradable poly (lactide/glycolide) copolymer;
(3) 0 to 90 v/v of a hydrophilic solvent; and
(4) 100 to 10 v/v of a lipophilic solvent.

19. A composition of claim 18 wherein in said compound of formula Ia
$R^1$ is bromine or $NR^4R^5$;
$R^4$ and $R^5$ are independently hydrogen or methyl; and
$R^6$ is halomethyl or haloethyl.

20. A composition of claim 17 wherein said compound of formula I is selected from the group consisting of:
(1) 6-amino-3-cyano-1-(2,6-dichloro-4-sulfurpentafluorophenyl)-4-(trifluoromethylthio)pyrazole;
(2) 6-amino-3-cyano-1-(2,6-dichloro-4-sulfurpentafluorophenyl)-4-(trifluoromethylsulfinyl)pyrazole;
(3) 6-amino-3-cyano-1-(2,6-dichloro-4-sulfurpentafluorophenyl)-4-(trifluoromethylsulfonyl)pyrazole;
(4) 6-amino-3-cyano-1-(2,6-dichloro-4-sulfurpentafluorophenyl)-4-(1,1-difluoroethylthio)pyrazole; and
(5) 6-bromo-3-cyano-1-(2,6-dichloro-4-sulfurpentafluorophenyl)-4-(trifluoromethylthio)pyrazole.

21. A composition of claim 13 which comprises:
(1) 1% to 10% of a compound of formula I;
(2) 1% to 10%% w/v of a biodegradable poly (lactide/glycolide) copolymer; and
(3) a mixture of hydrophilic and lipophilic solvents wherein the volume ratio of the hydrophilic and lipophilic solvents is from about 80:20 to about 10:90.

22. A composition of claim 14 which comprises:
(1) 1% to 10% of a compound of formula Ia;
(2) 1% to 10%% w/v of a biodegradable poly (lactide/glycolide) copolymer; and
(3) a mixture of hydrophilic and lipophilic solvents wherein the volume ratio of the hydrophilic and lipophilic solvents is from about 80:20 to about 10:90.

23. A composition of claim 22 wherein in said compound of formula Ia
$R^1$ is bromine or $NR^4R^5$;
$R^4$ and $R^5$ are independently hydrogen or methyl; and
$R^6$ is halomethyl or haloethyl.

24. A composition of claim 21 wherein said compound of formula I is selected from the group consisting of:
(1) 6-amino-3-cyano-1-(2,6-dichloro-4-sulfurpentafluorophenyl)-4-(trifluoromethylthio)pyrazole;
(2) 6-amino-3-cyano-1-(2,6-dichloro-4-sulfurpentafluorophenyl)-4-(trifluoromethylsulfinyl)pyrazole;
(3) 6-amino-3-cyano-1-(2,6-dichloro-4-sulfurpentafluorophenyl)-4-(trifluoromethylsulfonyl)pyrazole;
(4) 6-amino-3-cyano-1-(2,6-dichloro-4-sulfurpentafluorophenyl)-4-(1,1-difluoroethylthio)pyrazole; and
(5) 6-bromo-3-cyano-1-(2,6-dichloro-4-sulfurpentafluorophenyl)-4-(trifluoromethylthio)pyrazole.

25. A composition of claim 13 comprising
(1) 5 to 10% w/v of 6-amino-3-cyano-1-(2,6-dichloro-4-sulfurpentafluorophenyl)-4-(trifluoromethylthio)pyrazole;
(2) 5 to 10% w/v of a biodegradable poly (lactide/glycolide) copolymer; and
(3) glycerol formal:triacetin ratio from 50:50 to 0:100.

26. A method of controlling ectoparasitic infestation in a companion animal while avoiding or reducing the potential of vomition in the treated animal, which comprises injecting said animal with a pharmaceutical composition of claim 13.

27. A method of controlling ectoparasitic infestation in a companion animal while avoiding or reducing the potential of vomition in the treated animal, which comprises injecting said animal with a pharmaceutical composition of claim 17.

28. A method of controlling ectoparasitic infestation in a companion animal while avoiding or reducing the potential of vomition in the treated animal, which comprises injecting said animal with a pharmaceutical composition of claim 21.

29. A method of controlling ectoparasitic infestation in a companion animal while avoiding or reducing the potential of vomition in the treated animal, which comprises injecting said animal with a pharmaceutical composition of claim 25.

* * * * *